US011084731B2

United States Patent
Johanning et al.

(10) Patent No.: US 11,084,731 B2
(45) Date of Patent: Aug. 10, 2021

(54) METHOD FOR PRODUCING AMMONIA AND UREA IN A COMMON FACILITY

(71) Applicants: thyssenkrupp Industrial Solutions AG, Essen (DE); thyssenkrupp AG, Essen (DE)

(72) Inventors: Joachim Johanning, Oberhausen (DE); Yevgeny Makhynya, Mülheim an der Ruhr (DE)

(73) Assignees: thyssenkrupp Industrial Solutions AG, Essen (DE); thyssenkrupp AG, Essen (DE)

( * ) Notice: Subject to any disclaimer, the term of this patent is extended or adjusted under 35 U.S.C. 154(b) by 232 days.

(21) Appl. No.: 16/461,996

(22) PCT Filed: Nov. 13, 2017

(86) PCT No.: PCT/EP2017/079053
§ 371 (c)(1),
(2) Date: May 17, 2019

(87) PCT Pub. No.: WO2018/091410
PCT Pub. Date: May 24, 2018

(65) Prior Publication Data
US 2019/0322539 A1    Oct. 24, 2019

(30) Foreign Application Priority Data

Nov. 21, 2016  (DE) ................... 10 2016 122 374.3

(51) Int. Cl.
*C01C 1/04*    (2006.01)
*C01B 3/02*    (2006.01)
(Continued)

(52) U.S. Cl.
CPC ............ *C01C 1/0488* (2013.01); *C01B 3/025* (2013.01); *C01B 3/52* (2013.01); *C07C 273/04* (2013.01);
(Continued)

(58) Field of Classification Search
CPC ...... C01B 2203/068; C01B 2203/0415; C01B 3/025; C01B 3/52; C01C 1/0488; C07C 273/04; C07C 273/10
See application file for complete search history.

(56) References Cited

U.S. PATENT DOCUMENTS 3,310,376 A    3/1967  Cook
3,640,052 A    2/1972  Konoki
(Continued)

FOREIGN PATENT DOCUMENTS

DE    1 668 547 A    9/1971
DE    25 26 353 A    12/1975
(Continued)

OTHER PUBLICATIONS

English Translation of International Search Report issued in PCT/EP2017/079053, dated Jan. 17, 2018.

*Primary Examiner* — Jafar F Parsa
(74) *Attorney, Agent, or Firm* — thyssenkrupp North America, LLC (57) ABSTRACT

A process for preparing ammonia or ammonia and urea in a facility may involve compressing a crude synthesis gas stream that includes hydrogen, nitrogen, and carbon dioxide, washing a substream of the crude synthesis gas with ammonia to form a purified synthesis gas stream depleted of carbon dioxide and a condensate, synthesizing ammonia from the purified synthesis gas stream, and synthesizing urea from the condensate to form an aqueous urea composition. In the preparation of ammonia and urea, the crude synthesis (Continued)

gas stream may be, after being compressed, divided into a first synthesis gas substream and a second synthesis gas substream. In some instances, only the first synthesis gas substream is scrubbed with liquid ammonia.

4 Claims, 4 Drawing Sheets

(51) Int. Cl.
  *C01B 3/52* (2006.01)
  *C07C 273/04* (2006.01)
  *C07C 273/10* (2006.01)
(52) U.S. Cl.
  CPC .... *C07C 273/10* (2013.01); *C01B 2203/0415* (2013.01); *C01B 2203/068* (2013.01)

(56) References Cited

U.S. PATENT DOCUMENTS

| | | |
|---|---|---|
| 4,138,434 A | 2/1979 | Lagana |
| 4,320,103 A | 3/1982 | Pagani |
| 4,690,812 A | 9/1987 | Ranke |
| 6,340,451 B1 | 1/2002 | Pagani |

FOREIGN PATENT DOCUMENTS

| | | |
|---|---|---|
| DE | 26 13 102 C | 6/1982 |
| DE | 10 2015 210 801 A | 12/2016 |
| EP | 1 188 710 A | 3/2002 |
| JP | S60171202 A | 9/1985 |
| JP | 2000159519 A | 6/2000 |
| JP | 2000302743 A | 10/2000 |

METHOD FOR PRODUCING AMMONIA AND UREA IN A COMMON FACILITY

CROSS REFERENCE TO RELATED APPLICATIONS

This application is a U.S. National Stage Entry of International Patent Application Serial Number PCT/EP2017/079053, filed Nov. 13, 2017 which claims priority to German Patent Application No. DE 10 2016 122 374.3, filed Nov. 21, 2016, the entire contents of both of which are incorporated herein by reference.

FIELD

The present disclosure generally relates processes for preparing ammonia and urea in a joint facility or, as an alternative, only for preparing ammonia in such facility.

BACKGROUND

The industrial preparation of urea is at present based virtually exclusively on the high-pressure synthesis of ammonia ($NH_3$) and carbon dioxide ($CO_2$) at about 150 bar and about 180° C. Both starting materials generally come from an ammonia plant which is usually in the close vicinity of the urea plant concerned.

In the synthesis gas production of the ammonia plant, the carbon dioxide required for the urea synthesis is obtained as constituent of the crude synthesis gas after reforming. Since it would act as catalyst poison in the ammonia synthesis, the entire carbon dioxide, except for a limit value of 500 ppm, has to be separated off from the synthesis gas. Prior art for this is the use of regenerative gas scrubs, for which a large number of selectively acting solvents is available.

Carbon dioxide can also be separated off by means of an ammonia/water mixture or by means of ammonia. If the carbon dioxide is separated off by means of an ammonia/water mixture, it is predominantly chemically bound in the form of carbamate, hydrogencarbonate and carbonate ions in the solution.

Direct contact of the carbon dioxide with ammonia forms predominantly ammonium carbamate, and this is at the same time the starting material for the urea synthesis. There is only a theoretical storage possibility for ammonia carbamate, since it generally tends to degrade. This tendency is accelerated further by the presence of water.

The urea synthesis from ammonia and carbon dioxide is overall exothermic. It consists of the relatively strongly exothermic and comparatively fast reaction of the starting materials to form ammonium carbamate plus the significantly slower and endothermic further reaction to form urea and water. Good energy efficiency of the overall process can be achieved only when the heat of reaction liberated in the relatively strong exothermic carbamate formation reaction is at least partly utilized for the subsequent urea formation. The storage of the carbamate intermediate, on the other hand, implies cooling of the reaction mixture and leads to an additional consumption of energy. It is not possible to realize an advantageous overall solution in this way.

A number of concepts for process-side integration of, on the one hand, ammonia plant and, on the other, urea plant have been proposed in the past; the oldest concepts were published as early as the beginning of the 20th century. Most concepts are based on the separation of the carbon dioxide from the crude synthesis gas of the ammonia plant using ammonia produced in the process or using ammonia/water mixtures and further transfer of the product, which is predominantly present as ammonium carbamate, to the urea reactor.

However, none of these concepts have been realized industrially up to now. Reasons for this have not been made known.

According to the conventional concepts removal of carbon dioxide using ammonia produced in the process by operation of the ammonia plant and the urea plant is obviously possible only simultaneously. Here, the entire carbon dioxide formed during steam reforming must be passed on to the urea synthesis and reacted, which makes the overall facility inflexible and goes in the direction of a "balanced plant". In this case, it is not possible to produce further products, e.g. nitric acid, in appreciable amounts.

In addition, separate operation of one of the two plants, which is possible in the case of the conventional mode of operation, is difficult to realize. Furthermore, chemical problems such as additional introduction of water into the urea synthesis also occur, as a result of which the equilibrium of the urea formation reaction is influenced unfavorably.

In addition, no processes and no apparatuses which allow separate start-up of the ammonia plant or urea plant or flexible operation of integrated plants have hitherto been known.

DE 1 668 547 discloses a process for preparing $NH_3$ and urea, which is characterized in that $NH_3$ synthesis gas containing $CO_2$, $N_2$ and $H_2$ is introduced into a first zone which is maintained under such conditions that $CO_2$ is separated off from the synthesis gas in an ammonia-containing liquid and a condensate containing ammonium carbamate is obtained, and in that the residual ammonia synthesis gas is introduced into an ammonia synthesis zone and the condensate is introduced into a second zone which is maintained under conditions suitable for preparing urea from the condensate. This is a typical example of a fully integrated process in which no direct removal of $CO_2$ takes place.

DE 25 26 353 relates to an integrated process for preparing urea and $NH_3$. Here, the $NH_3$ is removed from the cycle gas by means of a water scrub. $CO_2$ is scrubbed out from the crude synthesis gas by means of a $NH_3/H_2O$ scrub.

DE 26 13 102 C2 discloses a process for the simultaneous preparation of $NH_3$ and urea, in which a gas mixture which is composed of $CO_2$, $N_2$ and $H_2$ and is obtained in the reforming of hydrocarbons with subsequent CO conversion is subjected to absorption of the carbon dioxide by means of ammonia solution, which is obtained in absorption of the ammonia from the ammonia synthesis by means of water, and the ammonium carbamate solution formed in this way is fed to the urea synthesis.

U.S. Pat. No. 4,138,434 relates to a process concept with integration of $NH_3$ synthesis and urea synthesis. Here, $CO_2$ is scrubbed out of the crude synthesis gas in two stages using aqueous ammonia to form ammonium carbamate. Residual $NH_3$ is stripped out by means of crude synthesis gas. Thermal stripping is carried out, with an ejector being used to compensate for pressure drops.

EP 1 188 710 A2 discloses a process for combined preparation of ammonia and of urea, in which an ammonia synthesis gas having a high content of carbon dioxide is firstly brought to a pressure suitable for the ammonia synthesis. The predominant proportion of carbon dioxide is removed by scrubbing with an aqueous ammonia solution, giving an ammonium carbamate solution which is fed to a urea reactor. Carbon monoxide is firstly removed from the stripped gas depleted in carbon dioxide in a methanation.

The gas saturated with ammonia after the methanation is combined with a product gas from an ammonia converter and then scrubbed with water in order to remove ammonia. The gas leaving the scrubbing apparatus contains some ammonia and some water, and these are removed by means of molecular sieves in an absorber. Downstream of the absorber, the purified gas is firstly introduced into a compressor and then into an ammonia synthesis unit. The product gas from the ammonia synthesis is scrubbed with water. The ammonia/water mixture obtained here is concentrated and, after the ammonia concentration has been increased, recirculated to the stage in which the ammonium carbamate solution is produced. In this known process, the entire crude synthesis gas stream is fed to an apparatus in which carbamate is produced from the carbon dioxide present in the crude synthesis gas by reaction with an ammonia/water mixture. Only after this removal of the carbon dioxide is the gas stream then fed to a methanation and then a scrub using water in order to remove ammonia from the synthesis gas stream. This is then followed by further separation steps before ammonia is synthesized from the purified synthesis gas.

The known fully integrated processes and apparatuses are thus not satisfactory in every respect and there is a need for improved processes and apparatuses. In particular, the energy consumption for carbon dioxide compression should be reduced and/or the outlay in terms of apparatus for the plant should be reduced overall.

Thus a need exists for an improved process and an improved plant for preparing ammonia and urea, which can be used for the synthesis of urea and ammonia in a joint facility and overcome the disadvantages of the prior art.

DETAILED DESCRIPTION

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting "a" element or "an" element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present disclosure generally relates to processes for preparing ammonia and urea in a joint facility or, as an alternative, only for preparing ammonia in this facility. In one example process, a crude synthesis gas stream that contains at least the gases hydrogen, nitrogen, and carbon dioxide is firstly compressed, then at least one substream of the crude synthesis gas is washed with ammonia, forming a purified synthesis gas stream depleted in carbon dioxide and also a condensate, where ammonia is synthesized from the purified synthesis gas stream which is depleted in carbon dioxide and urea is synthesized from the condensate to form an aqueous urea composition. The present disclosure also generally relates to plants for synthesizing ammonia and urea, in which the starting materials of the urea synthesis can be provided entirely from plants for the preparation of ammonia.

In the preparation of ammonia and urea in the joint facility, the crude synthesis gas stream is, according to the invention, after compression divided into two substreams, namely a first synthesis gas substream and a second synthesis gas substream, with only the first synthesis gas substream being scrubbed with liquid ammonia. This measure has the advantage that the second synthesis gas substream, which also contains carbon dioxide, can be utilized, for example, for stripping an aqueous urea solution which is obtained in the urea synthesis. It is thus not necessary for additional carbon dioxide to be introduced into the plant for such stripping. The preparation of ammonia and urea in a joint facility is also referred to as "integrated synthesis of the urea and ammonia" in the technical field.

When mention is made in the present application of division into two substreams, this means that the synthesis gas stream is, with the composition staying the same, divided into two substreams which are then, after the division, conveyed further via separate routes and are treated further in different ways in the subsequent process. This division is thus not a separation of the synthesis gas stream in such a way that individual gas components are separated off from the synthesis gas stream and two synthesis gas streams having different compositions are produced as a result.

The percentage division of the synthesis gas stream into the two substreams can of course vary within a wide range, i.e. it is not necessarily the case that a division into two substreams having equal proportions by volume occurs.

The solution proposed according to the invention avoids the disadvantages of the above-described known processes and also allows separate start-up and separate operation of the two subplants of the facility and also operation of each of these under less than full load. This is achieved by means of further plant parts which will be described below. In addition, a reduction in the capital costs and an improvement in the specific energy consumption are achieved by the solution according to the invention.

It has surprisingly been found that the process of the invention makes actual omission of the apparatus for compression of carbon dioxide, as is required in the conventional urea synthesis, possible. In addition, the apparatus for the carbon dioxide scrub as is required in the conventional ammonia synthesis is dispensed with when carrying out the process of the invention.

Since the steam consumption for the carbon dioxide compressor is saved, a significant reduction in the energy consumption for the total facility can be obtained. In addition, the omission of the carbon dioxide compressor including its auxiliary apparatuses (drive turbine, intermediate cooler, oil system, etc.) and the carbon dioxide scrub leads to a very substantial reduction in the capital costs of the plant.

Furthermore, an additional introduction of water into the urea synthesis is largely avoided by means of the process of the invention. This is because the carbon dioxide can be driven off from the scrubbing solution, which is formed on scrubbing with water and ammonia, at elevated temperature and a pressure level slightly above the urea synthesis pressure. With increasing desorption pressure, it is possible to obtain the carbon dioxide in sufficient purity for the urea synthesis and, in particular, the proportion of water is significantly reduced.

The quantity of heat required for the desorption of the carbon dioxide and also the quantity of steam required for the additional requirement of the synthesis gas compressor, and also further quantities of steam and heat, can be made available by means of limited modifications of the steam system in integrated ammonia/urea plants. Furthermore, the heat consumed by the carbon dioxide scrub in the conventional process can be utilized by the steam system.

A further embodiment of the invention provides a process for the preferably integrated preparation of ammonia and urea, optionally only ammonia, where the process of the invention comprises the following steps:
a. provision of a crude synthesis gas stream comprising hydrogen, nitrogen and carbon dioxide and optionally relative small proportions of methane, argon, carbon dioxide and possibly helium;
b. optionally division of the crude synthesis gas stream in a first crude synthesis gas stream and a third crude synthesis gas stream;
c. optionally scrubbing of the third crude synthesis gas stream with a scrubbing solution comprising water and ammonia to form a prepurified synthesis gas stream depleted in carbon dioxide and a scrubbing solution enriched in carbon dioxide;
d. optionally driving-off of carbon dioxide from the scrubbing solution enriched in carbon dioxide to form a compressed carbon dioxide stream;
e. optionally combination of the prepurified synthesis gas stream with the third crude synthesis gas stream to form a combined synthesis gas stream;
f. compression of the optionally combined synthesis gas stream to form a compressed synthesis gas stream;
g. division of the compressed synthesis gas stream into a first synthesis gas stream and a second synthesis gas stream;
h. provision of a composition comprising a liquid ammonia;
i. scrubbing of the first synthesis gas stream and optionally of the stripping gas stream from step (k) and also optionally of the compressed carbon dioxide stream from step (d) with the composition comprising liquid ammonia to form a purified synthesis gas stream depleted in carbon dioxide and a condensate;
j. synthesis of
i.($j_1$) ammonia from the purified synthesis gas stream depleted in carbon dioxide; and
ii.($j_2$) urea from the condensate to form an aqueous urea composition;
iii.(k) optionally stripping of the aqueous urea composition from step (j2) by means of the second synthesis gas stream from step (g).

In this possible variant of the invention, the crude synthesis gas stream is divided before compression into two substreams to form a third (crude) synthesis gas substream and a crude synthesis gas stream which is fed to a compressor, where the third (crude) synthesis gas substream is scrubbed in a scrubbing apparatus with a scrubbing solution comprising water and ammonia to form a prepurified synthesis gas stream depleted in carbon dioxide and a scrubbing solution enriched in carbon dioxide, with the prepurified synthesis gas stream then being combined again with the crude synthesis gas stream and fed together with the latter to the compressor.

Carbon dioxide can be driven off from the scrubbing solution in a desorption apparatus at a pressure which is above the level of the urea synthesis.

The process of the invention serves to prepare ammonia and urea. Here, the integrated preparation of ammonia and urea is preferably carried out, i.e. at least part of the ammonia produced and/or at least part of the carbon dioxide formed in the preparation of the ammonia are used for the subsequent preparation of urea. However, it is also possible according to the invention to prepare exclusively ammonia at least temporarily.

The process of the invention makes the synthesis of ammonia and urea in a fully integrated process possible. For the purposes of the description, the term "ammonia plant" refers in the following to all apparatuses which are used separately for the synthesis of ammonia and the term "urea plant" refers to all apparatuses which are used separately for the synthesis of urea.

The concept according to the invention makes four different modes of operation possible:
i. operation of both plants in the fully integrated mode at full load or part load (case I);
ii. sole operation of the ammonia plant (case II);
iii. operation of both plants in an alternative fully integrated mode (case III);
iv. sole operation of the ammonia plant in an alternative fully integrated mode (case IV).

That is to say, the ammonia plant is in all four cases operated in full-load or part-load operation, while at the same time the urea plant is operated either with full load or part load (cases I and III) or is not operated at all (cases II and IV).

In step (a) of the process of the invention, a crude synthesis gas stream which comprises hydrogen, nitrogen and carbon dioxide and optionally relatively small proportions of methane, argon, carbon dioxide and possibly helium is provided.

In step (a) of the process of the invention, a synthesis gas which is referred to according to the invention as "crude synthesis gas stream" is provided. This crude synthesis gas stream differs in terms of its composition, in particular in respect of its content of carbon dioxide, from the "prepurified synthesis gas stream" obtained in step (c) and from the "purified synthesis gas stream" obtained in step (i). Fundamentally, the content of carbon dioxide in the synthesis gas stream decreases continually ever further during the course of the process of the invention.

Here, $H_2$, $N_2$ and $CO_2$ are preferably the main constituents of the crude synthesis gas stream. The crude synthesis gas stream can optionally comprise further, preferably inert, components such as methane, argon, carbon monoxide and/or helium. The crude synthesis gas stream is preferably obtained from hydrocarbons, more preferably from natural gas and water in the form of steam. Suitable processes for producing such a crude synthesis gas stream are known to those skilled in the art and reference may in this respect to, for example, all of A. Nielsen, I. Dybkjaer, Ammonia—Catalysis and Manufacture, Springer Berlin 1995, chapter 6, pages 202-326; M. Appl, Ammonia. Principles and Industrial Practice, WILEY-VCH Verlag GmbH 1999. In a preferred embodiment, at least part of the crude synthesis gas stream is provided by steam reforming and/or by autothermal reforming.

The synthesis gas stream provided in step (a) of the process of the invention can have been subjected to conventional treatment measures for synthesis gas, e.g. helium removal, natural gas desulfurization and/or conversion of CO into $CO_2$.

The crude synthesis gas stream provided in step (a) has preferably been subjected beforehand at least to one such conversion of CO into $CO_2$.

However, the crude synthesis gas stream has particularly preferably not been subjected beforehand to any further treatment measures which in the conventional provision of synthesis gas usually follow such a conversion of CO into $CO_2$, e.g. $CO_2$ removal or final purification. Possibilities for final purification in conventional processes are, in particular, methanation, methanolization, cryogenic purification (nitrogen scrub), copper scrub or combinations thereof. However, the crude synthesis gas stream provided in step (a) has preferably not been subjected to such further treatment measures.

The content of $CO_2$ in the crude synthesis gas stream is preferably in the range from 1% by volume to 25% by volume, more preferably from 10% by volume to 20% by volume.

The crude synthesis gas stream is preferably subjected to heat integration. The heat integration is particularly preferably carried out after the conversion of CO into $CO_2$.

In step (b) of the process of the invention, the crude synthesis gas stream is, in an embodiment of the process, divided into a first crude synthesis gas stream and a second crude synthesis gas stream.

In a preferred embodiment, the first crude synthesis gas stream is larger than the second crude synthesis gas stream. In another preferred embodiment, the second crude synthesis gas stream is larger than the first crude synthesis gas stream.

In a preferred embodiment, the relative ratio of the first crude synthesis gas stream to the second crude synthesis gas stream is in the range from 1:20 to 1:1, more preferably from 1:15 to 1:1, even more preferably from 1:10 to 1:1. In another preferred embodiment, the relative ratio of the second crude synthesis gas stream to the first crude synthesis gas stream is in the range from 1:20 to 1:1, more preferably from 1:15 to 1:1, even more preferably from 1:10 to 1:1. In a further preferred embodiment, the relative ratio of the first crude synthesis gas stream to the second crude synthesis gas stream is in the range from 1:20 to 20:1, more preferably from 1:15 to 15:1, even more preferably from 1:10 to 10:1. The ratio can be changed during the course over time of the process.

In step (c) of the process of the invention, the first crude synthesis gas stream is, in an embodiment of the process, scrubbed with a scrubbing solution comprising water and ammonia. Here, a prepurified synthesis gas stream depleted in carbon dioxide and a scrubbing solution enriched in carbon dioxide are formed.

Suitable scrubbing columns for scrubbing synthesis gas with a scrubbing solution comprising water and ammonia are known to those skilled in the art.

In the scrubbing solution for step (c), which comprises water and ammonia, the proportion of ammonia is preferably in the range from 1 to 50% by weight, more preferably in the range from 5 to 45% by weight, even more preferably in the range from 10 to 40% by weight, most preferably in the range from 15 to 35% by weight and in particular in the range from 20 to 25% by weight.

The scrubbing solution enriched in carbon dioxide is preferably present in liquid form and can be separated off from the prepurified synthesis gas stream depleted in carbon dioxide. The carbon dioxide in the scrubbing solution is preferably predominantly chemically bound in the form of carbamate, hydrogencarbonate and carbonate.

The prepurified synthesis gas stream depleted in carbon dioxide preferably contains not more than 5% by volume, more preferably not more than 10% by volume, even more preferably not more than 15% by volume, particularly preferably not more than 20% by volume, of carbon dioxide.

According to the invention, the proportion of carbon dioxide in the prepurified synthesis gas stream is smaller than in the crude synthesis gas stream.

In step (d) of the process of the invention, carbon dioxide is, in one embodiment of the process, driven off from the scrubbing solution enriched in carbon dioxide, forming a compressed carbon dioxide stream.

The carbon dioxide is preferably driven off from the scrubbing solution from step (c) at elevated temperature and a pressure level slightly above the urea synthesis pressure. Studies have shown that it is possible to obtain the carbon dioxide at this high pressure level in sufficient purity for the urea synthesis and to be able to reduce the proportion of water, in particular, significantly. If the carbon dioxide stream is fed in a further step to the urea synthesis, an additional introduction of water into the urea synthesis is largely avoided.

In a preferred embodiment, the quantity of heat required for the desorption of the carbon dioxide can be made available by means of limited modifications of the steam system in ammonia/urea facilities. Even more preferably, the heat which would be consumed by the carbon dioxide scrub in a conventional process can be utilized by the steam system.

The compressed carbon dioxide stream is preferably formed in an apparatus, namely the desorption column, which differs from the apparatus, namely the absorption column, in which step (c) of the process of the invention takes place. The scrubbing column for step (c) and the desorption column for step (d) are combined in a joint apparatus, namely the ammonia-water scrub.

The compressed carbon dioxide stream preferably contains at least 10% by volume, more preferably at least 15% by volume, even more preferably at least 20% by volume, particularly preferably at least 25% by volume, of carbon dioxide. In addition, the compressed carbon dioxide stream can comprise ammonia and water.

In step (e) of the process of the invention, the prepurified synthesis gas stream from step (c) is, in an embodiment of the process, combined with the second crude synthesis gas stream from step (b) to form a combined synthesis gas stream.

In a preferred embodiment, the prepurified synthesis gas stream is larger than the second crude synthesis gas stream. In a preferred embodiment, the prepurified synthesis gas stream is smaller than the second crude synthesis gas stream.

In a preferred embodiment, the relative ratio of the prepurified synthesis gas stream and the second crude synthesis gas stream is in the range from 1:20 to 1:1, more preferably from 1:15 to 1:1, even more preferably from 1:10 to 1:1. In another preferred embodiment, the relative ratio of the prepurified synthesis gas stream and the second crude synthesis gas stream is in the range from 20:1 to 1:1, more preferably from 15:1 to 1:1, even more preferably from 10:1 to 1:1. In a further preferred embodiment, the relative ratio of the prepurified synthesis gas stream and the second crude synthesis gas stream is in the range from 1:20 to 20:1, more preferably from 1:15 to 15:1, even more preferably from 1:10 to 10:1. The ratio can be changed during the course over time of the process.

The proportion of carbon dioxide in the combined synthesis gas stream is preferably smaller than in the crude synthesis gas stream but higher than in the prepurified first synthesis gas stream.

The content of carbon dioxide in the combined synthesis gas stream is preferably at least 5% by volume, more preferably at least 10% by volume, even more preferably at least 15% by volume, particularly preferably at least 20% by volume, of carbon dioxide. In a further embodiment, the combined synthesis gas stream can comprise further, preferably inert, components such as methane, argon, carbon monoxide and/or helium.

In step (f) of the process of the invention, the combined synthesis gas stream from step (e) is compressed to form a compressed synthesis gas stream.

After step (f) of the process of the invention, all further steps (g) to (i) and the urea synthesis in step ($j_2$) are preferably carried out at a common pressure level of in each case at least 145 bar or at a pressure which is slightly above the synthesis pressure for urea. Here, pressure drops as usually occur in the industrial synthesis of urea are possible in carrying out the further steps (g) to (i) and ($j_2$). The pressure level achieved in step (f) of the process of the invention is preferably sufficiently high to overcome these pressure drops.

However, the ammonia synthesis in step ($j_1$) can preferably also be carried out at a significantly higher pressure level, e.g. from 200 to 350 bar.

In a further preferred embodiment, all further steps (g) to (j) after step (f) of the process of the invention are carried out at a common pressure level. More preferably, no further compression of the gas streams is carried out subsequent to step (f) to step (j) of the process of the invention.

Particular preference is given to an embodiment in which the gas stream is not compressed again by means of a $CO_2$ compressor subsequent to step (d) before carrying out the urea synthesis.

In step (g) of the process of the invention, the compressed synthesis gas stream from step (f) is divided into a first synthesis gas stream and a second synthesis gas stream.

In a preferred embodiment, the first synthesis gas stream is larger than the second synthesis gas stream. In a preferred embodiment, the first synthesis gas stream is smaller than the second synthesis gas stream.

In a preferred embodiment, the relative ratio of the first synthesis gas stream and the second synthesis gas stream is in the range from 1:20 to 1:1, more preferably from 1:15 to 1:1, even more preferably from 1:10 to 1:1. In another preferred embodiment, the relative ratio of the first synthesis gas stream and the second synthesis gas stream is in the range from 20:1 to 1:1, more preferably from 15:1 to 1:1, even more preferably from 10:1 to 1:1. In a further preferred embodiment, the relative ratio of the first synthesis gas stream and the second synthesis gas stream is in the range from 1:20 to 20:1, more preferably from 1:15 to 15:1, even more preferably from 1:10 to 10:1. The ratio can be changed during the course over time of the process.

In step (h) of the process of the invention, a composition comprising liquid ammonia is provided.

The liquid ammonia for step (h) is preferably provided in its entirety by means of step ($j_1$).

In another preferred embodiment, the aqueous urea composition from step ($j_2$) is purified further in step (k) by stripping with the second synthesis gas stream from step (g). The second synthesis gas stream is subsequently preferably combined in step (i) with the first synthesis gas stream and optionally the compressed carbon dioxide stream from step (d).

In step (i) of the process of the invention, the first synthesis gas stream from step (g), optionally the stripping gas stream from step (k) and optionally the compressed carbon dioxide stream from step (d) are scrubbed with the composition comprising liquid ammonia from step (h). Here, a purified synthesis gas stream depleted in carbon dioxide and a condensate are formed.

Suitable scrubbing columns for scrubbing synthesis gas with a composition comprising liquid ammonia are known to those skilled in the art.

The condensate is present in liquid form and can be separated from the purified synthesis gas stream. In a preferred embodiment, the condensate is separated from the purified synthesis gas stream in the scrubbing column in which step (i) is carried out.

In the condensate, the carbon dioxide is preferably predominantly present in the form of ammonium carbamate which is the starting material for the urea synthesis. In addition, the condensate can comprise other ammonium salts such as ammonium hydrogencarbonate and ammonium carbonate and also unreacted $NH_3$ and $CO_2$.

The purified synthesis gas stream depleted in carbon dioxide can still contain residues of $CO_2$ and/or CO. The purified synthesis gas stream preferably contains not more than 0.05 mol % of carbon dioxide, more preferably not more than 0.04 mol %, particularly preferably not more than 0.03 mol %. According to the invention, the proportion of carbon dioxide in the purified synthesis gas stream is smaller than in the first synthesis gas stream. The proportion of carbon dioxide in the purified synthesis gas stream is below 500 ppm.

In a preferred embodiment, the carbamate condenser required in the conventional urea synthesis is replaced by scrubbing with the composition comprising liquid ammonia in step (i) of the process of the invention.

In step (j) of the process of the invention, ammonia and urea are synthesized. In step ($j_1$), ammonia is synthesized from the purified synthesis gas stream depleted in carbon dioxide from step (i). In step ($j_2$), urea is synthesized from the condensate from step (i), forming an aqueous urea composition.

The synthesis of urea in step ($j_2$) preferably occurs in a conventional urea reactor, the structure of which is known to a person skilled in the art.

In a preferred embodiment, the synthesis of the urea in step ($j_2$) comprises only the endothermic partial reaction in which the ammonium carbamate is converted into urea and water.

Since the ammonium carbamate has already been formed in step (i), the exothermic reaction to form ammonium carbamate can no longer completely cover the energy requirement for the endothermic reaction, so that the urea reactor preferably has to be additionally heated from the outside.

The synthesis of urea in step ($j_2$) is preferably carried out at a pressure in the range from 100 to 300 bar, more preferably in the range from 120 to 200 bar, even more preferably in the range from 140 to 160 bar.

The synthesis of ammonia from the purified synthesis gas stream in step ($j_1$) is preferably carried out in a conventional ammonia reactor, the structure of which is known to a person skilled in the art.

In a preferred embodiment, the purified synthesis gas stream from step (i) is subjected to a further purification step, e.g. methanation, before the ammonia synthesis. These processes are prior art for the synthesis of ammonia and known to a person skilled in the art.

Preference is given to at least part of the gaseous $NH_3$ formed in the ammonia reactor being condensed out, for which purpose the gas stream preferably passes firstly through a heat exchanger and subsequently through a condensation apparatus. Here, the gas stream is cooled, preferably to temperatures in the range from $+5°$ C. to $-40°$ C., more preferably in the range from $0°$ C. to $-35°$ C., in the range from $-5°$ C. to $-33°$ C. or in the range from $-10°$ C. to $-30°$ C.

A conventional $CO_2$ scrub in the ammonia plant is preferably omitted in the process of the invention; this is replaced by scrubbing of the crude synthesis gas stream with scrubbing solutions comprising water and ammonia as per step (c) and/or liquid ammonia as per step (i). Likewise, a $CO_2$ compressor which is otherwise required for the urea synthesis is dispensed with.

In a preferred embodiment, the process of the invention comprises the additional step (k) in which the aqueous urea composition from step ($j_2$) is stripped by means of the second synthesis gas stream from step (g). A stripping gas stream and a purified aqueous urea solution are formed here.

The aqueous urea composition produced in step ($j_2$) comprises essentially urea, water, ammonium carbamate, other ammonium salts such as ammonium hydrogencarbonate and ammonium carbonate and also unreacted $NH_3$ and $CO_2$. The ammonium carbamate should be decomposed thermally and the $NH_3$ and the $CO_2$ have to be removed from the solution and can then be reused for the reaction process for the urea synthesis. The removal is preferably achieved as per step (k) by stripping with the second synthesis gas stream from step (g). Stripping processes are prior art for urea plants and are known to a person skilled in the art.

The scrubbing in step (i) of the process of the invention is preferably carried out using a composition which is obtained by combining
the composition comprising liquid ammonia provided previously in step (h) and
the stripping gas stream from step (k).

In a further preferred embodiment of the process of the invention, the stripping gas stream from step (k) is combined in step (i) with the first synthesis gas stream and optionally at least part of the compressed carbon dioxide stream from step (d) and combined with the composition comprising liquid ammonia from step (h).

The constituents of the stripping gas stream are preferably fed back to the urea synthesis by the combining with the composition comprising liquid ammonia.

In a particularly preferred embodiment, the following components are reacted in the scrub as per step (i) to give a purified synthesis gas stream and a condensate:
the composition comprising liquid ammonia previously provided in step (h),
the first synthesis gas stream from step (g),
preferably the stripping gas stream from step (k), and
optionally at least part of the compressed carbon dioxide stream from step (d).

In a preferred embodiment, the process of the invention comprises the additional step (i*) in which the purified synthesis gas stream depleted in carbon dioxide from step (i) is subjected to methanation to form a high-purity synthesis gas stream and the high-purity synthesis gas stream is transferred to the synthesis of ammonia as per step ($j_1$). Suitable methods for hydrogenating CO and $CO_2$ to methane are known to a person skilled in the art.

The content of $CO_2$ in the high-purity synthesis gas stream from step (i*) is, according to the invention, smaller than in the purified synthesis gas stream and is preferably in the range up to 500 ppm, more preferably below 500 ppm. Even more preferably, the high-purity synthesis gas stream additionally comprises essentially only $H_2$ and $N_2$ and inert gases.

In a preferred embodiment, the high-purity synthesis gas stream is fed to the synthesis of $NH_3$ in step ($j_1$).

In a preferred embodiment, the process of the invention comprises the additional step (d*) in which at least part of the compressed carbon dioxide stream from step (d) is combined with the composition comprising liquid ammonia from step (h).

In a preferred embodiment of the process of the invention, the total amount of the compressed carbon dioxide stream from step (d) is combined with the composition comprising liquid ammonia from step (h) and optionally the other gas streams as per step (i). This process variant is preferably employed in the operation of the urea plant in the fully integrated mode (case I) either in part load or in full load.

In a preferred embodiment, the process of the invention comprises the additional step (l) in which at least part of the compressed carbon dioxide stream from step (d) is discharged.

In a preferred embodiment of the process of the invention, the total amount of the compressed carbon dioxide stream from step (d) is discharged. This process variant is preferably used in the sole operation of the ammonia plant (case II).

In a further preferred embodiment, the compressed carbon dioxide stream is passed through a turbine before discharge.

Even more preferably, the water and the ammonia present in the compressed carbon dioxide stream are separated off and/or recovered before discharge. Methods for performing this are known to a person skilled in the art.

In a particularly preferred embodiment, the compressed carbon dioxide stream is discharged into the air, particularly preferably after the compressed carbon dioxide stream has been depressurized and purified. Methods of performing this are known to a person skilled in the art.

In the case of operation according to case (II), only an ammonia synthesis but not a urea synthesis takes place, with step (i) preferably not being carried out.

In the case of a sole synthesis of ammonia, the steps (b), (e), (g), (i) and (k) are particularly preferably not carried out and in step (1) it is not the combined synthesis gas stream from step (e) but instead a synthesis gas stream formed by methanation as per step (i*) which is compressed and from which ammonia is then synthesized.

The present invention further provides a plant for preparing ammonia and urea or alternatively (depending on requirements) only ammonia, which comprises the following components which are in active communication with one another:
an apparatus configured for providing a crude synthesis gas stream comprising hydrogen, nitrogen and carbon dioxide and optionally relatively small proportions of methane, argon, carbon dioxide and possibly helium;

at least one compressor configured for compressing the crude synthesis gas stream to form a compressed synthesis gas stream;

at least one scrubbing column configured for scrubbing the compressed synthesis gas stream with a composition comprising ammonia to form a purified synthesis gas stream depleted in carbon dioxide and a condensate;

at least one first reactor configured for synthesizing ammonia from the purified synthesis gas stream;

at least one second reactor configured for synthesizing urea from the condensate to form an aqueous urea composition, wherein, according to the invention, the plant further comprises at least one apparatus which is located downstream of the compressor and is configured for dividing the compressed synthesis gas stream from the compressor into a first synthesis gas stream and a second synthesis gas stream, where a first conduit via which only the first synthesis gas stream can be fed to the scrubbing column leads from the dividing apparatus to the scrubbing column, where the plant further comprises a stripper and a second conduit via which only the second synthesis gas stream can be fed to the stripper leads from the dividing apparatus to the stripper, where a conduit going from the second reactor to the stripper, via which the aqueous urea composition can be conveyed from the second reactor to the stripper, is provided.

In the plant according to the invention, only ammonia can be prepared in the same facility when there is no demand for urea. Here, the plant according to the invention differs from solutions known from the prior art in respect of its flexibility. In addition, the plant of the invention can advantageously be operated only in part load and a specific mode of operation in a start-up phase and/or in a shut-down phase of the process can be provided.

The plant of the invention preferably further comprises a second dividing apparatus which is located upstream of the compressor in the flow direction and by means of which the crude synthesis gas stream can be divided into two substreams, with a first conduit for a first substream leaving from the second dividing apparatus to the compressor and a second conduit for a third substream leaving from the second dividing apparatus to a scrubbing apparatus which is configured for scrubbing the third substream of the crude synthesis gas with a scrubbing solution comprising water and ammonia to form a prepurified synthesis gas stream depleted in carbon dioxide and a scrubbing solution enriched in carbon dioxide and for driving off carbon dioxide from the scrubbing solution enriched in carbon dioxide to form a compressed carbon dioxide stream, where means for combining the prepurified third synthesis gas substream from the scrubbing apparatus downstream of the scrubbing apparatus and upstream of the compressor with the first synthesis gas substream to form a combined synthesis gas stream which can be fed via a conduit to the compressor are provided.

A preferred further embodiment of the invention provides a plant for the preferably integrated preparation of ammonia and urea, where the plant comprises the following components which are in active communication with one another:

(A) an apparatus configured for providing the crude synthesis gas stream comprising hydrogen, nitrogen and carbon dioxide and optionally relatively small proportions of methane, argon, carbon dioxide and possibly helium;

(B) an apparatus configured for dividing the crude synthesis gas stream into a first crude synthesis gas stream and a third crude synthesis gas stream;

(C) an apparatus configured for scrubbing the third crude synthesis gas stream from (B) with a scrubbing solution comprising water and ammonia to form a prepurified synthesis gas stream depleted in carbon dioxide, a scrubbing solution enriched in carbon dioxide and a compressed carbon dioxide stream;

(D) means for combining the prepurified third synthesis gas stream from (C) with the first crude synthesis gas stream from (B) to form a combined synthesis gas stream;

(E) a compressor configured for compressing a synthesis gas stream, for example the combined synthesis gas stream from (D), to form a compressed synthesis gas stream;

(F) an apparatus configured for dividing the compressed synthesis gas stream from (E) into a first synthesis gas stream and a second synthesis gas stream;

(G) a scrubbing column configured for scrubbing the first synthesis gas stream from (F) with a composition comprising liquid ammonia to form a purified synthesis gas stream depleted in carbon dioxide and a condensate;

(H) a reactor configured for synthesizing ammonia from the combined synthesis gas stream from (G); and (I) a reactor configured for synthesizing urea from the condensate from (G) to form an aqueous urea composition.

All preferred embodiments described in connection with the process of the invention apply analogously to the plant of the invention and will therefore not be repeated at this juncture.

The plant of the invention comprises an apparatus configured for providing a crude synthesis gas stream. This preferably comprises a steam reformer and/or an autothermal reformer. If the plant comprises an autothermal reformer, the amount of $CO_2$ formed in the autothermal reformer can be controlled by variation of reaction parameters such as the pressure or the steam/carbon ratio. A preferred embodiment of the plant additionally comprises an apparatus configured for converting CO into $CO_2$ and/or an apparatus configured for heat integration.

The plant of the invention preferably comprises an apparatus configured for dividing the crude synthesis gas stream into a first crude synthesis gas stream and a third crude synthesis gas stream. This apparatus is preferably configured so that the volume ratio of the crude synthesis gas streams can be varied while carrying out the process of the invention.

The plant of the invention preferably comprises an apparatus configured for scrubbing the third crude synthesis gas stream from (B) with a scrubbing solution comprising water and ammonia to form a prepurified synthesis gas stream depleted in carbon dioxide and a scrubbing solution enriched in carbon dioxide and for driving carbon dioxide off from the scrubbing solution enriched in carbon dioxide to form a compressed carbon dioxide stream.

The plant of the invention preferably comprises a means for combining the prepurified synthesis gas stream from (C) with the first crude synthesis gas stream from (B) to form a combined synthesis gas stream.

The plant of the invention comprises a compressor configured for compressing a synthesis gas stream, for example the combined synthesis gas stream from (D), to form a compressed synthesis gas stream.

In a preferred embodiment, the plant does not comprise any further compressor. The apparatus particularly preferably does not comprise any $CO_2$ compressor customary in the conventional urea synthesis.

The plant of the invention comprises an apparatus configured for dividing the compressed synthesis gas stream from (E) into a first synthesis gas stream and a second synthesis gas stream.

The plant of the invention comprises a scrubbing column configured for scrubbing the first synthesis gas stream from (F) with a composition comprising liquid ammonia to form a purified synthesis gas stream depleted in carbon dioxide and a condensate.

The plant of the invention comprises a reactor configured for synthesizing ammonia from the purified synthesis gas stream from (G).

The plant of the invention comprises a reactor configured for synthesizing urea from the condensate from (G) to form an aqueous urea composition.

The plant of the invention preferably does not comprise any apparatus for the conventional $CO_2$ scrub, as is frequently used after the CO conversion in conventional plants for the synthesis of $NH_3$, and also no $CO_2$ compressor including its entire periphery which is otherwise additionally required for the urea synthesis.

In a preferred embodiment, the plant of the invention additionally comprises the following components:
- an apparatus (J) configured for stripping the aqueous urea composition from (I) with the second synthesis gas stream from (F) to form a stripping gas stream and a purified aqueous urea solution;
- means (K) for combining the stripping gas stream from (J) with the composition comprising liquid ammonia from (G); and/or
- an apparatus (L) configured to effect the methanation of the purified synthesis gas stream depleted in carbon dioxide from (G) to form a high-purity synthesis gas stream.

In a further preferred embodiment, the plant of the invention additionally comprises the following components:
- means (M) for combining at least part of the compressed carbon dioxide stream from (C) with the composition comprising liquid ammonia from (G);
- means (N) for combining at least part of the ammonia from (H) with the composition comprising liquid ammonia from (G); and/or
- an apparatus (O) configured for discharging at least part of the compressed carbon dioxide stream from step (C).

The apparatus (O) preferably comprises a turbine through which the compressed carbon dioxide stream is conveyed before discharge. The apparatus (O) even more preferably also comprises an apparatus configured for separating off and/or recovering the water and the ammonia present in the compressed carbon dioxide stream before discharge. A further preferred embodiment of apparatus (O) comprises an apparatus configured for releasing the carbon dioxide into the air.

All preferred embodiments described in connection with the process of the invention apply analogously to the preferred embodiments of the plant and will therefore not be repeated at this juncture.

In a preferred embodiment of the concept according to the invention, only the ammonia plant is operated without simultaneous operation of the urea plant (case II). In this case, the carbon dioxide is preferably, as in the conventional process, released into the air or alternatively passed to a further neighboring urea plant.

In the preferred sole ammonia synthesis (case II) using the plant of the invention, the process comprises, according to the invention, the following steps:
- provision of a crude synthesis gas stream comprising hydrogen, nitrogen and carbon dioxide and optionally relatively small proportions of methane, argon, carbon dioxide and possibly helium;
- scrubbing of the crude synthesis gas stream with a scrubbing solution comprising water and ammonia to form a prepurified synthesis gas stream depleted in carbon dioxide and a scrubbing solution enriched in carbon dioxide;
- driving-off of carbon dioxide from the scrubbing solution enriched in carbon dioxide to form a compressed carbon dioxide stream;
- methanation of the prepurified synthesis gas stream to form a high-purity synthesis gas stream;
- transfer of the high-purity synthesis gas stream into a compressor configured for compressing the combined synthesis gas stream to form a compressed high-purity synthesis gas stream;
- transfer of the compressed high-purity synthesis gas stream into the reactor configured for synthesizing ammonia; and
- synthesis of ammonia.

What has been said above in respect of the corresponding process steps for the process of the invention applies analogously to the sole ammonia synthesis.

The plant of the invention is particularly suitable for carrying out the process of the invention. A further aspect of the invention therefore provides for the use of the plant of the invention in the process of the invention.

Figure 1:
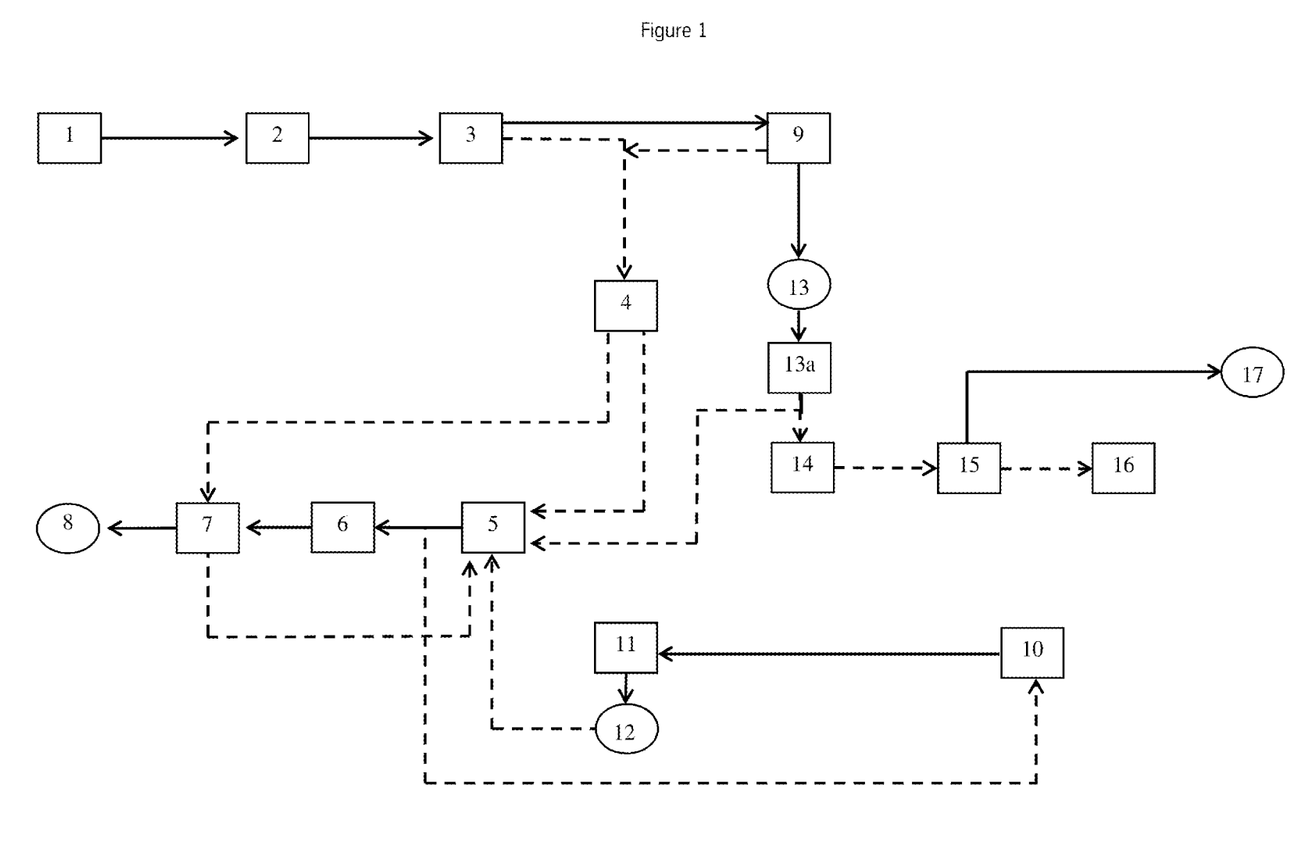
FIG. 1 is a schematic view of an example process in which an ammonia plant and a urea plant are operated in a fully integrated full-load or part-load mode (case I).

FIG. 1 schematically illustrates a preferred variant of the process of the invention, in which the ammonia plant and the urea plant are operated in the fully integrated full-load or part-load mode (case I). Here, broken lines indicate streams which according to the invention are variable, i.e. can disappear in particular modes of operation.

The crude synthesis gas is provided after it has preferably passed through a reformer (1) and/or preferably a CO conversion (2) and/or preferably a heat integration (3). The crude synthesis gas is then optionally divided into a first crude synthesis gas stream and a third crude synthesis gas stream, which can preferably have different sizes during the course over time of the process. The third crude synthesis gas stream is optionally scrubbed in an apparatus (9) by means of a scrubbing solution comprising water and ammonia. Here, a synthesis gas stream prepurified by removal of carbon dioxide and a scrubbing solution (13) enriched in carbon dioxide are formed.

The carbon dioxide is optionally driven off from the scrubbing solution in the apparatus (13a) to form a compressed carbon dioxide stream, and this at a pressure which is slightly above the level of the urea synthesis and is high enough to compensate for the pressure drops up to the actual urea synthesis.

The prepurified synthesis gas stream is optionally combined with the first crude synthesis gas stream. The combined synthesis gas stream which is optionally formed in this way is compressed in a synthesis gas compressor (4) to a pressure which is slightly above the level of the urea synthesis and is high enough to compensate for the pressure drops up to the actual urea synthesis.

The compressed synthesis gas stream formed in this way is then divided into a first synthesis gas stream and a second synthesis gas stream. For the subsequent scrubbing of the first synthesis gas stream in a scrubbing column (5) by means of a composition comprising a liquid ammonia, liquid ammonia (12) is provided.

The liquid ammonia is preferably entirely provided from the ammonia synthesis (11). Part of the composition can preferably also be provided from a stripper (7). The scrubbing of the first synthesis gas stream in the scrubbing column (5) by means of a composition comprising liquid ammonia forms a purified synthesis gas stream depleted in carbon dioxide and a condensate. The compressed carbon dioxide stream can preferably also be transferred, in its entirety or in part, into the scrubbing column (5) and be reacted there.

For the ammonia synthesis, the purified synthesis gas stream depleted in carbon dioxide is then fed into an ammonia reactor (11) for the synthesis. A high-purity synthesis gas stream can preferably be formed beforehand from the purified synthesis gas stream in an apparatus (10) configured to effect methanation, and this is then transferred into the ammonia reactor (11) for the synthesis.

For the urea synthesis, the condensate from the scrubbing column (5) is transferred into a urea reactor (6) and an aqueous urea composition is formed. A stripping gas stream and a purified aqueous urea solution are preferably formed from this urea composition in a stripper (7), and the purified aqueous urea solution is then preferably converted into granular urea (8) by means of further process steps known to those skilled in the art.

In a preferred embodiment, the second synthesis gas stream and the urea composition are fed into the stripper (7). In a further preferred embodiment, part of the carbon dioxide stream at high pressure, which is not fed into the scrubbing column (5), is conveyed through a turbine (14), then conveyed through an apparatus (15) configured for separating off ammonia by absorption in water and subsequently released as purified carbon dioxide stream (17) into the environment. The ammonia in the ammonia-laden aqueous solution from the ammonia separation (15) is removed by desorption from the aqueous solution in an apparatus (16) configured for recovering ammonia and is recirculated to the process at a suitable point.

Figure 2:
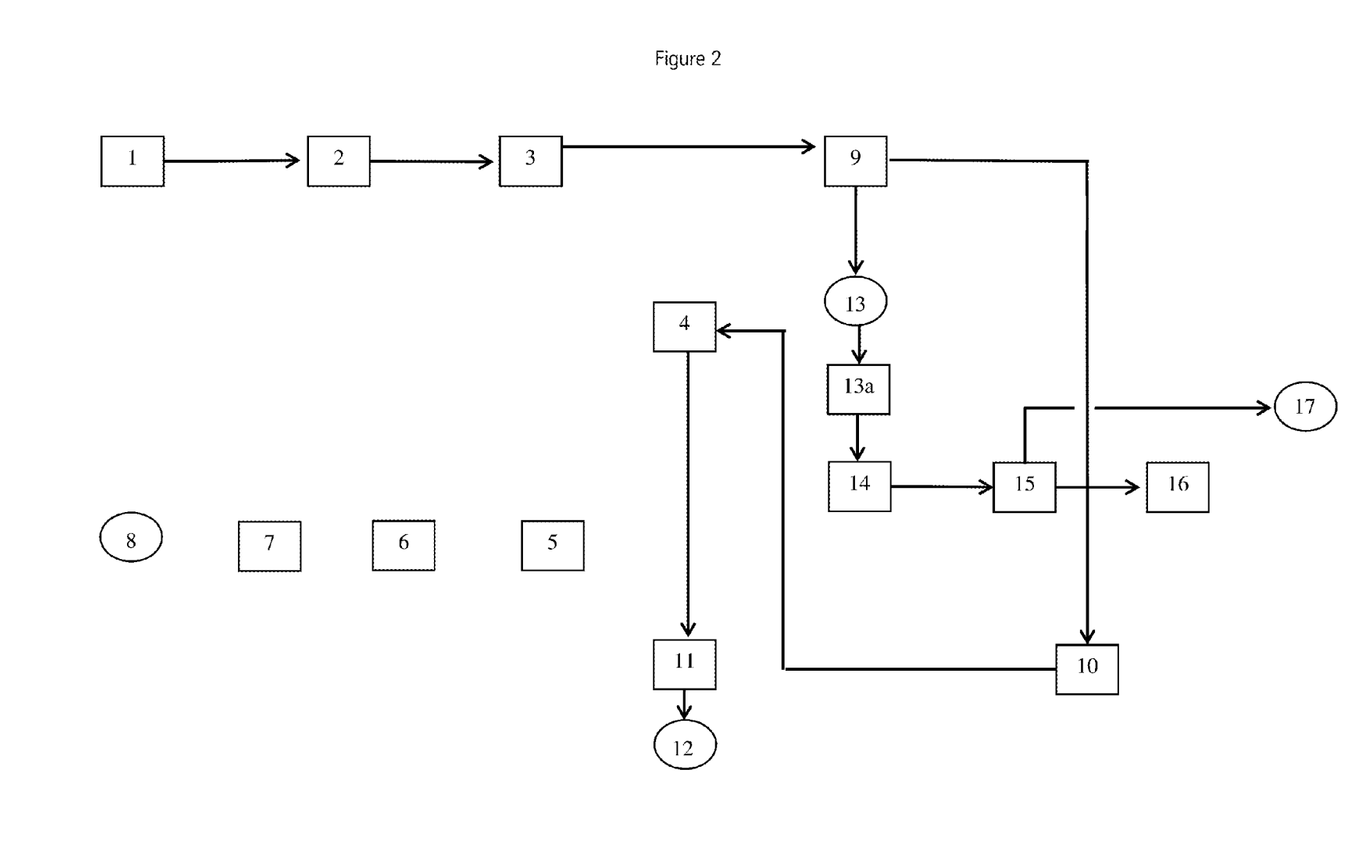
FIG. 2 is a schematic view of an example process in which only ammonia (case II) is synthesized by way of an apparatus.

FIG. 2 schematically illustrates a preferred variant of the process of the invention, in which only ammonia (case II) is synthesized by means of the apparatus of the invention.

In contrast to FIG. 1 (case I), the crude synthesis gas stream is not divided. The crude synthesis gas stream is scrubbed with a scrubbing solution comprising water and ammonia in an apparatus (9). Here, a synthesis gas stream prepurified by removal of carbon dioxide and a scrubbing solution (13) enriched in carbon dioxide are formed. The carbon dioxide is driven off from the scrubbing solution to form a compressed carbon dioxide stream in the apparatus (13a).

The compressed carbon dioxide stream is, after the desorption (13a), conveyed through a turbine (14), then through an apparatus (15) configured for separating off ammonia by absorption in water and subsequently released as purified carbon dioxide stream (17) into the environment. The ammonia in the ammonia-laden aqueous solution from the ammonia separation (15) is removed in an apparatus (16) configured for recovering ammonia by desorption from the aqueous solution and is recirculated to the process. The prepurified synthesis gas stream from (9) is transferred into an apparatus (10) configured for effecting methanation and a high-purity synthesis gas stream is formed. The high-purity synthesis gas stream is compressed in a synthesis gas compressor (4) and then transferred into the ammonia reactor (11) for the ammonia synthesis.

Figure 3:
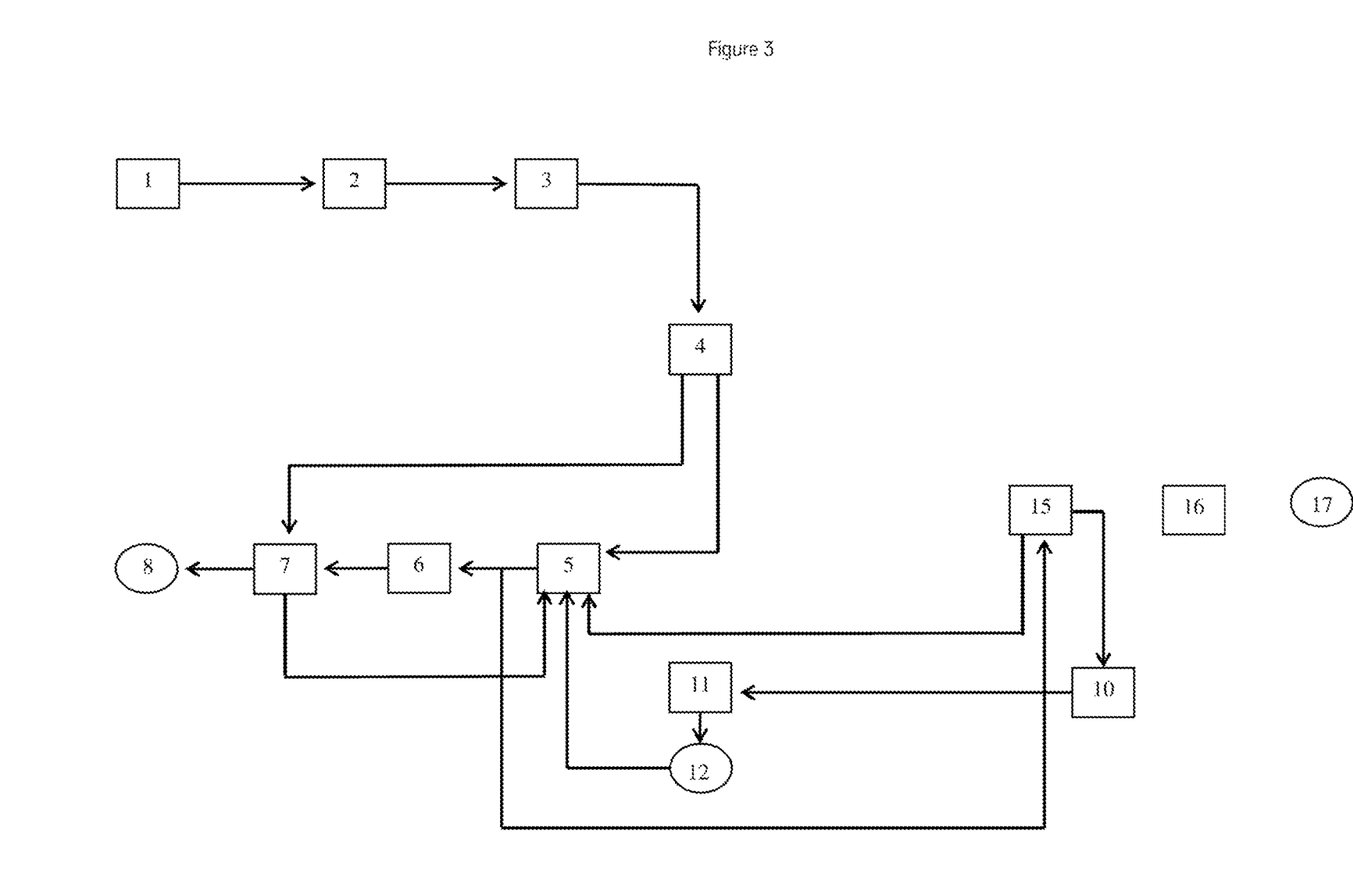
FIG. 3 is a schematic view of another example process in which an ammonia plant and a urea plant are operated in an alternative fully integrated mode (case III).

FIG. 3 schematically illustrates a further preferred variant of the process of the invention, in which the ammonia plant and the urea plant are operated in an alternative fully integrated mode (case III).

The crude synthesis gas is provided after it has preferably passed through a reformer (1) and/or preferably a CO conversion (2) and/or preferably a heat integration (3). In contrast to FIG. 1 (case I), the entire crude synthesis gas is then compressed in a synthesis gas compressor (4) to a pressure which is slightly above the level of the urea synthesis and is high enough to compensate for the pressure drops up to the actual urea synthesis. The compressed crude synthesis gas stream is divided and a second part is transferred into a stripper (7).

The first part is transferred into the scrubbing column (5) with a composition comprising liquid ammonia. The liquid ammonia in this composition is provided entirely from the ammonia synthesis (11). The gaseous product from the stripper (7) is also transferred completely into the scrubbing column (5) and provided as part of the composition of the scrubbing column (5). The scrubbing of the first part of the crude synthesis gas stream and of the gaseous product from the stripper (7) in the scrubbing column (5) forms a purified synthesis gas stream depleted in carbon dioxide and a condensate. For the urea synthesis, the condensate is transferred into a urea reactor (6) and an aqueous urea composition is formed. A stripping gas stream and a purified aqueous urea solution are then formed from this urea composition in a stripper (7).

The purified synthesis gas stream is transferred into an apparatus (15) which is configured for separating off ammonia and absorbing water. The ammonia separated off there is likewise recirculated to the scrubbing column (5). A high-purity synthesis gas stream is formed from the remaining gas in an apparatus (10) configured for effecting methanation, and this is then transferred into the ammonia reactor (11) for the ammonia synthesis.

Figure 4:
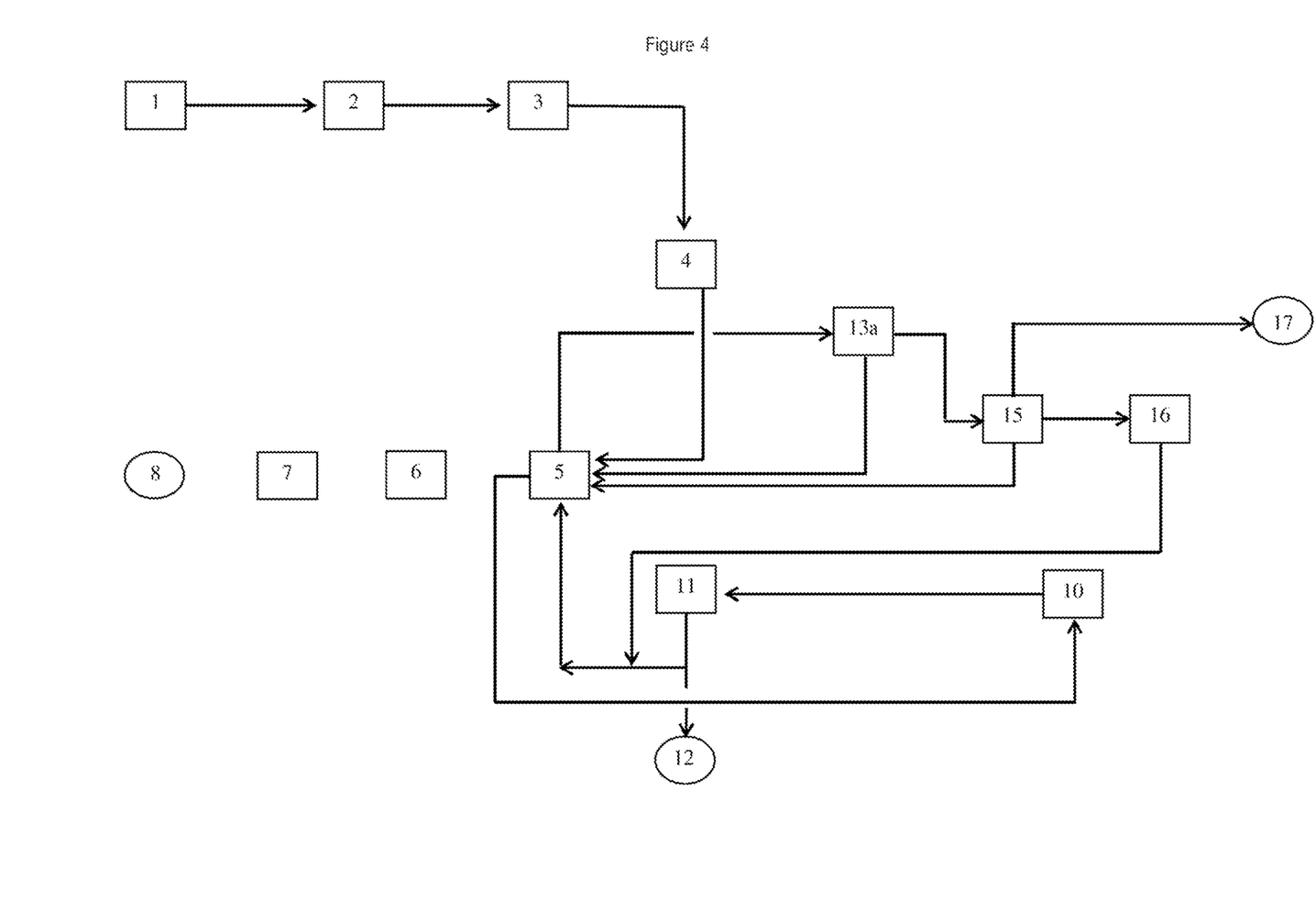
FIG. 4 is a schematic view of still another example process in which only ammonia is synthesized by way of an apparatus in an alternative fully integrated mode (case IV).

FIG. 4 schematically illustrates a further preferred variant of the process of the invention, in which only ammonia is synthesized by means of the apparatus of the invention in an alternative fully integrated mode (case IV).

The crude synthesis gas stream is, as in FIG. 3, not divided and firstly compressed in a synthesis gas compressor (4) to a pressure which is slightly above the level of the urea synthesis and is high enough to compensate for the pressure drops up to the actual urea synthesis. In contrast to the mode of operation according to case III depicted in FIG. 3, the compressed crude synthesis gas stream is not divided but instead transferred into the scrubbing column (5). In the scrubbing column (5), the crude synthesis gas stream is brought into contact with a composition comprising liquid ammonia and a purified synthesis gas stream depleted in carbon dioxide and a condensate are formed. The liquid ammonia (12) in this composition is provided in its entirety from the ammonia synthesis (11).

The purified synthesis gas stream is transferred into an apparatus (10) configured for effecting methanation and a high-purity synthesis gas stream is formed. The high-purity synthesis gas stream is then transferred into the ammonia reactor (11) for the ammonia synthesis and ammonia (12) is synthesized.

The condensate enriched in carbon dioxide from the scrubbing column (5) is fed into a desorption (13a) and a gaseous carbon dioxide stream and a condensate depleted in carbon dioxide are obtained. The condensate depleted in carbon dioxide is recirculated back into the scrubbing column (5). The carbon dioxide stream is transferred into an apparatus (15) in which the ammonia still present in the carbon dioxide stream is separated off, e.g. by absorption in water, before the purified carbon dioxide stream (17) can be released into the environment. The ammonia which has been separated off is removed from the aqueous solution by desorption in the apparatus (16) configured for recovering ammonia and is recirculated to the scrubbing column (5).

LIST OF REFERENCE NUMERALS

1 Reformer
2 CO conversion

3 Heat integration
4 Synthesis gas compressor
5 Scrubbing apparatus/scrubbing column with a composition comprising liquid ammonia
6 Urea reactor
7 Stripper
8 Urea
9 Apparatus with a scrubbing solution comprising water and ammonia
10 Methanation
11 Ammonia reactor
12 Ammonia
13 Scrubbing solution at high pressure enriched in carbon dioxide
13a Desorption
14 Turbine
15 Ammonia removal/absorption in water
16 Ammonia recovery/desorption from water
17 Discharge of carbon dioxide

What is claimed is:

1. A plant for preparing ammonia and urea or for preparing ammonia, the plant comprising:
    an apparatus configured to provide a crude synthesis gas stream comprising hydrogen, nitrogen, and carbon dioxide;
    a compressor configured to compress the crude synthesis gas stream to form a compressed synthesis gas stream;
    a scrubbing column configured to scrub the compressed synthesis gas stream with a composition comprising ammonia to form a purified synthesis gas stream depleted of carbon dioxide and a condensate;
    a first reactor configured to synthesize ammonia from the purified synthesis gas stream;
    a second reactor configured to synthesize urea from the condensate to form an aqueous urea composition;
    a first dividing apparatus downstream of the compressor for dividing the compressed synthesis gas stream into a first synthesis gas stream and a second synthesis gas stream;
    a first conduit via which only the first synthesis gas stream can be fed to the scrubbing column, the first conduit leading from the first dividing apparatus to the scrubbing column;
    a stripper;
    a second conduit via which only the second synthesis gas stream can be fed to the stripper, the second conduit leading from the first dividing apparatus to the stripper; and
    a third conduit extending from the second reactor to the stripper, wherein the aqueous urea composition is conveyable from the second reactor to the stripper via the third conduit.

2. The plant of claim 1 comprising:
    a second dividing apparatus disposed upstream of the compressor, wherein by way of the second dividing apparatus the crude synthesis gas stream is dividable into a first substream and a second substream, wherein a fourth conduit for the first substream extends from the second dividing apparatus to the compressor, wherein a fifth conduit for the second substream extends from the second dividing apparatus to a scrubbing apparatus configured to scrub the second substream of the crude synthesis gas with a first scrubbing solution comprising water and ammonia to form a pre-purified synthesis gas stream depleted of carbon dioxide and a second scrubbing solution enriched in carbon dioxide and for driving off carbon dioxide from the second scrubbing solution to form a compressed carbon dioxide stream; and
    means for combining a pre-purified third synthesis gas substream from the scrubbing apparatus downstream of the scrubbing apparatus and upstream of the compressor with a first synthesis gas substream to form a combined synthesis gas stream that can be fed via a conduit to the compressor.

3. The plant of claim 1 comprising at least one of:
    a sixth conduit for feeding a stripping gas stream from the stripper to the scrubbing column; or
    an apparatus disposed upstream of the first reactor for synthesis of ammonia and configured to effect methanation of a purified synthesis gas stream depleted of carbon dioxide from the scrubbing column to form a high-purity synthesis gas stream.

4. The plant of claim 1 comprising a series of apparatuses configured to remove, separate off, and recover ammonia and water from at least part of a compressed carbon oxide stream obtained downstream of the scrubbing apparatus.

* * * * *